United States Patent [19]
Randad et al.

[11] Patent Number: 5,925,780
[45] Date of Patent: Jul. 20, 1999

[54] 2, 5-DIAMINO-3, 4-DISUBSTITUTED-1, 6-DIPHENYLHEXANE ISOSTERES COMPRISING BENZAMIDE, SULFONAMIDE AND ANTHRANILAMIDE SUBUNITS AND METHODS OF USING SAME

[75] Inventors: Ramnarayan S. Randad; John W. Erickson, both of Frederick, Md.

[73] Assignee: The United States of America as represented by the Department of Health and Human Services, Washington, D.C.

[21] Appl. No.: 09/039,669

[22] Filed: Mar. 16, 1998

Related U.S. Application Data

[62] Division of application No. 08/359,612, Dec. 20, 1994, Pat. No. 5,728,718.

[51] Int. Cl.$^6$ .................................................. C07C 261/00
[52] U.S. Cl. ............................................................... 560/24
[58] Field of Search .................................................. 560/24

[56] References Cited

U.S. PATENT DOCUMENTS

| | | | |
|---|---|---|---|
| 3,838,145 | 9/1974 | Altermatt | 514/66 |
| 4,051,196 | 9/1977 | Wells et al. | 260/857 |
| 4,568,666 | 2/1986 | McCullagh et al. | 514/20 |
| 5,142,056 | 8/1992 | Kempf et al. | 546/265 |
| 5,180,744 | 1/1993 | Hanson et al. | 514/616 |
| 5,214,129 | 5/1993 | Luly et al. | 530/331 |
| 5,254,724 | 10/1993 | Bergeron, Jr. | 560/312 |
| 5,256,677 | 10/1993 | Sham et al. | 514/351 |
| 5,272,175 | 12/1993 | Hansen, Jr. et al. | 514/486 |
| 5,354,866 | 10/1994 | Kempf et al. | 546/265 |

FOREIGN PATENT DOCUMENTS

| | | |
|---|---|---|
| 0 402 646 | 5/1990 | European Pat. Off. |
| 0 541 467 A2 | 5/1992 | European Pat. Off. |
| 0 580 402 A2 | 7/1993 | European Pat. Off. |
| WO 91/18866 | 12/1991 | WIPO . |

OTHER PUBLICATIONS

Bone et al., "X–ray Crystal Structure of the HIV Protease Complex with L–700, 417, an Inhibitor with Pseudo $C_2$ Symmetry," *J. Am. Chem. Soc.*, 113:9382–9384 (Jul., 1991).
*Chemical Abstracts*, vol. 115, No. 5, Abstract 50304r, Aug. 5, 1991, p. 914.
*Chemical Abstracts*, vol. 116, No. 21, Abstract 214, 913m, May 25, 1992, p. 792.
Erickson et al., "Design, Activity, and 2.8 A Crystal Structure of a $C_2$ Symmetric Inhibitor Complexed to HIV–1 Protease," *Science*, 249:527–533 (Aug. 1990).
Flentge et al., "Symmetry–Based Inhibitors of HIV Protease With High Oral Bioavailability," Abstract, Amer. Chem. Society Mtg. (1994).
Green et al., "Symmetry–Based HIV Protease Inhibitors: Structure–Based Design of P2 Amino Acid Replacements," Abstract, Amer. Chem. Society Mtg. (1993).
Kempf et al., "Antiviral and Pharmacokinetic Properties of $C_2$ Symmetric Inhibitors of the Human Immunodeficiency Virus Type 1 Protease," *Antimicrobial Agents and Chomotherapy*, 35(11):2209–2214 (Nov. 1991).
Kempf et al., "Design of Orally Bioavailable, Symmetry–Based Inhibitors of HIV Protease," *Bioorganic & Medicinal Chemistry*, 2(9):847–858 (1994).
Kempf et al., "Structure–Based, $C_2$ Symmetric Inhibitors of HIV Protease," *Journal of Medicinal Chemistry*, 33(10):2687–2689 (1990).
Kempf et al., "Structure–Based Inhibitors of HIV Protease," Recent Advances in the Chem. of Anti–Infective Agents, Bently et al., eds. Royal Society of Chem., Cambridge (1993) pp. 297–313.
Kempf et al., "Symmetry–Based Inhibitors of HIV Protease. Structure–Activity Studies of Acylated 3,4–Diamino–1, 5–diphenyl–3–hydroxypentane and 2,5–Diamino–1, 6–diphenylhexane–3, 4–diol," *J. Med. Chem*, 36:320–330 (1993).
Randad et al., "Symmetry–Based HIV Protease Inhibitors: Rational Design of Hydroxybenzamide as a Novel $P_2$ Replacement," Abstract, AIDS Structure Mtg., NIH (1994).

*Primary Examiner*—Zinna Northington Davis
*Attorney, Agent, or Firm*—Leydig, Voit & Mayer, Ltd.

[57] ABSTRACT

The present invention provides 2,5-diamino-3,4-disubstituted-1,6-diphenylhexane (DAD) isosteres comprising benzamide, sulfonamide and anthranilamide subunits, a pharmaceutical composition comprising such compounds, a method of using such compounds to treat retroviral, specifically HIV and more specifically HIV-1 and HIV-2, infections in mammals, particularly humans, a method of synthesizing asymmetric DAD isosteres comprising benzamide, sulfonamide and anthranilamide subunits, and a method of using such compounds to assay new compounds for antiretroviral activity.

1 Claim, No Drawings

5,925,780

2, 5-DIAMINO-3, 4-DISUBSTITUTED-1, 6-DIPHENYLHEXANE ISOSTERES COMPRISING BENZAMIDE, SULFONAMIDE AND ANTHRANILAMIDE SUBUNITS AND METHODS OF USING SAME

This application is a divisional of Ser. No. 08/359,612 filed Dec. 20, 1994, now U.S. Pat. No. 5,728,718.

TECHNICAL FIELD OF THE INVENTION

This invention relates to 2,5-diamino-3,4-disubstituted-1, 6-diphenylhexane (DAD) isosteres comprising novel, non-peptidic and achiral subunits and, more particularly, to DAD isosteres comprising benzamide, sulfonamide and anthranilamide subunits. This invention also relates to a pharmaceutical composition comprising such compounds, a method of using such compounds to treat retroviral infections in mammals, a method of using such compounds in antiretroviral activity assays, and a method of synthesizing asymmetric DAD isosteres comprising benzamide, sulfonamide and anthranilamide subunits.

BACKGROUND OF THE INVENTION

Acquired immune deficiency syndrome (AIDS) is a fatal disease, reported cases of which have increased dramatically within the past several years. Estimates of reported cases in the very near future also continue to rise dramatically. Consequently, there is a great need to develop drugs and vaccines to combat AIDS.

The AIDS virus was first identified in 1983. It has been known by several names and acronyms. It is the third known T-lymphocyte virus (HTLV-III), and it has the capacity to replicate within cells of the immune system, causing profound cell destruction. The AIDS virus is a retrovirus, a virus that uses reverse transcriptase during replication. This particular retrovirus is also known as lymphadenopathy-associated virus (LAV), AIDS-related virus (ARV) and, most recently, as human immunodeficiency virus (HIV). Two distinct families of HIV have been described to date, namely HIV-1 and HIV-2. The acronym HIV will be used herein to refer to HIV viruses generically.

Specifically, HIV is known to exert a profound cytopathic effect on the CD4+ helper/inducer T-cells, thereby severely compromising the immune system. HIV infection also results in neurological deterioration and, ultimately, in the death of the infected individual.

The field of viral chemotherapeutics has developed in response to the need for agents effective against retroviruses, in particular HIV. There are many ways in which an agent can exhibit anti-retroviral activity. For example, HIV requires at least four viral proteins for replication: reverse transcriptase (RT), protease (PR), transactivator protein (TAT), and regulator of virion-protein expression (REV). Accordingly, viral replication theoretically could be inhibited through inhibition of any one or all of the proteins involved in viral replication.

The PR processes polyprotein precursors into viral structural proteins and replicative enzymes. This processing is essential for the assembly and maturation of fully infectious virions. Accordingly, the design of PR inhibitors is an important therapeutic goal in the treatment of AIDS.

Anti-retroviral agents, such as 3'-azido-2',3'-dideoxythymidine (AZT), 2',3'-dideoxycytidine (ddC), and 2',3'-dideoxyinosine (ddI) are known to inhibit RT. There also exist antiviral agents that inhibit TAT.

Nucleoside derivatives, such as AZT, are the only clinically active agents that are currently available for antiviral therapy. Although very useful, the. utility of AZT and related compounds is limited by toxicity and insufficient therapeutic indices for fully adequate therapy.

Numerous classes of potent peptidic inhibitors of PR have been designed using the natural cleavage site of the precursor polyproteins as a starting point. These inhibitors typically are peptide substrate analogs in which the scissile $P_1$—$P_1$, amide bond has been replaced by a nonhydrolyzable isostere with tetrahedral geometry (Moore et al., *Perspect. Drug Dis. Design*, 1, 85 (1993); Tomasselli et al., *Int. J. Chem. Biotechnology*, 6 (1991); Huff, *J. Med. Chem.*, 34, 2305 (1991); Norbeck et al., *Ann. Reports Med. Chem.*, 26, 141 (1991); Meek, *J. Enzyme Inhibition*, 6, 65 (1992)). Although these inhibitors are effective in preventing the retroviral PR from functioning, the inhibitors suffer from some distinct disadvantages. Generally, peptidomimetics often make poor drugs due to their potential adverse pharmacological properties, i.e., poor oral absorption, poor stability and rapid metabolism (Plattner et al., *Drug Discovery Technologies*, Clark et al., eds., Ellish Horwood, Chichester, England (1990)). Furthermore, since the active site of the PR is hindered, i.e., has reduced accessibility as compared to the remainder of the PR, the ability of the inhibitors to access and bind in the active site of the PR is impaired, and those that do bind are generally poorly water-soluble, causing distinct problems in drug delivery.

The design of HIV-1 protease inhibitors based on the transition state mimetic concept has led to the generation of a variety of peptide derivatives highly active against viral replication in vitro (Erickson et al., *Science*; 249, 527–533 (1990); Kramer et al., *Science*, 231, 1580–1584 (1986); McQuade et al., *Science*, 247, 454–456 (1990); Meek et al., *Nature (London)*, 343, 90–92 (1990); Roberts et al., *Science*, 248, 358–361 (1990)). These active agents contain a non-hydrolyzable, dipeptide isostere such as hydroxyethylene (McQuade et al., supra; Meek et al., *Nature (London)*, 343, 90–92 (1990); Vacca et al., *J. Med. Chem.*, 34, 1225–1228 (1991)) or hydroxyethylamine (Rich et al., *J. Med. Chem.*, 33, 1285–1288 (1990); Roberts et al., *Science*, 248, 358–361 (1990)) as an active moiety which mimics the putative transition state of the aspartic protease-catalyzed reaction. Twofold ($C_2$) symmetric inhibitors of HIV protease represent another class of potent HIV protease inhibitors which were created by Erickson et al. on the basis of the three-dimensional symmetry of the enzyme active site (Erickson et al., supra). A-77003 and other compounds designed on the $C_2$ symmetry are undergoing clinical trials in humans (Kempf et al., *Antimicrob. Agents Chemother.*, 35, 2209 (1991); Kempf et al., U.S. Pat. No. 5,142,056). However, peptidic compounds, such as those described by Kempf et al., which contain valinyl subunits, could undergo racemization to inactive enantiomers, i.e., enantiomers which do not demonstrate antiretroviral activity, and would, therefore, be expected to be. of limited utility.

Recent studies, however, have revealed the emergence of mutant strains of HIV in which the protease is resistant to the $C_2$ symmetric inhibitors (Otto et al., *PNAS USA*, 90, 7543 (1993); Ho et al.,*J. Virology*, 68, 2016–2020 (1994); Kaplan et al., *PNAS USA*, 91, 5597–5601 (1994)). In one study, the most abundant mutation found in response to A7703 was Arg to Gln at position 8 (R8Q), which strongly affects the $S_3/S_{3'}$ subsite of the protease binding domain. Shortening the $P_3/P_{3'}$ residues of A-77003 results in inhibitors that are equipotent towards both wild-type and R8Q mutant proteases (Majer et al., 13*th American Peptide Symposium*, Edmonton, Canada (1993)). Inhibitors have been truncated to P$_2$/P$_2'$ without significant loss of activity (Lyle et al., *J. Med. Chem.*, 34, 1230 (1991); Bone et al., *J. Am. Chem. Soc.*, 113, 9382 (1991)). These results suggest that inhibitors can be truncated and yet maintain the crucial interactions necessary for strong binding. The benefits of such an approach include the elimination of two or more peptide bonds, the reduction of molecular weight, the diminishment of the potential for recognition by degradative enzymes, and the improvement of activity against certain drug-resistant strains.

The use of HIV protease inhibitors in combination with agents that have different antiretroviral mechanisms (e.g., AZT, ddI and ddT) also has been described. For example, synergism against HIV-1 has been observed between certain C$_2$ symmetric HIV inhibitors and AZT (Kageyama et al., *Antimicrob. Agents Chemother.*, 36, 926–933 (1992)).

The usefulness of currently available HIV protease inhibitors in the treatment of AIDS has been limited by relatively short plasma half-life, poor oral bioavailability, and the technical difficulty of scale-up synthesis (Meek et al., *J. Enzyme Inhibition*, 6, 65–98 (1992)). There remains an urgent need, therefore, for retroviral protease inhibitors that do not suffer from the disadvantages of currently available retroviral protease inhibitors as well as effective methods of treating retroviral infection, in particular HIV infection, involving the administration of novel antiretroviral agents alone and in combination with other antiretroviral therapies.

Accordingly, it is an object of the present invention to provide antiretroviral compounds, specifically retroviral protease inhibitors, that are resistant to viral and mammalian protease degradation and which, therefore, have improved plasma half-life and oral bioavailability. It is a related object of the present invention to provide a method of treating retroviral, specifically HIV and more specifically HIV-1 and HIV-2, infection in a mammal, specifically a human, involving the administration of one or more of the antiretroviral compounds of the present invention alone or in combination with one or more other, currently available, antiretroviral therapies. Accordingly, it is also an object of the present invention to provide pharmaceutical compositions comprising the antiretroviral compounds. Another object of the present invention is to provide a method of using such compounds to assay new compounds for antiretroviral activity and a method of synthesizing the present inventive asymmetric antiretroviral compounds so as to enable scale-up synthesis. These and other objects and advantages of the present invention, as well as additional inventive features, will be apparent from the description of the invention provided herein.

BRIEF SUMMARY OF THE INVENTION

The present invention provides symmetric and asymmetric antiretroviral compounds of formula:

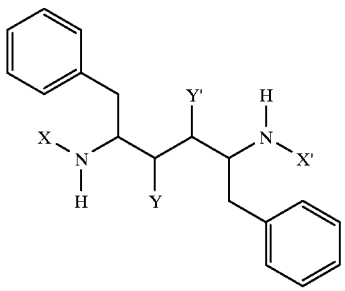

wherein the stereochemistry of each of the benzyl groups on the carbon atoms adjacent to the carbon atoms with the Y and Y' substituents is R or S. Y and Y' are the same or different and are R-hydroxyl, S-hydroxyl, R-amino, S-amino or hydrogen. X and X' are the same or different and are

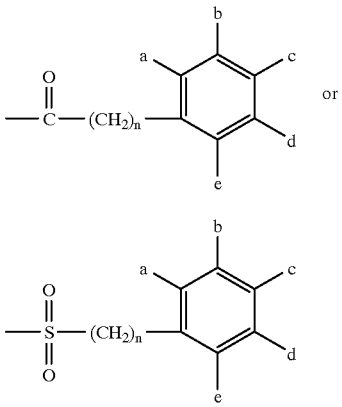

wherein n is 0 or 1. a–e are the same or different and are hydrogen, hydroxyl, halogen, sulfhydryl, carboxyl, carboxamido, a substituted or unsubstituted amino, OR''', a C$_{1-6}$ substituted or unsubstituted straight or branched chain alkyl, a (CH$_2$)$_m$Z'', an O(CH$_2$)$_m$Z'', or an N(R) (CH$_2$)$_m$Z''. R''' is a C$_{1-6}$ substituted or unsubstituted straight or branched chain alkyl. Z'' is phenyl, pyridinyl, morpholinyl, piperazinyl, indolyl, quinolinyl, isoquinolinyl, thiazolyl, benzimidazolyl, aminothiazolyl, piperidinyl or oxazolyl. Also provided is a pharmaceutical composition comprising one or more of the above-described compounds alone or in combination with one or more other currently available antiretroviral compounds. A method of treating a retroviral, specifically HIV and more specifically HIV-1 and HIV-2, infection in a mammal, particularly a human, is further provided wherein a compound as described above is administered alone or in combination with one or more other currently available antiretroviral therapies. Also further provided are a method of using such compounds to assay new compounds for antiretroviral activity and a method of synthesizing asymmetric compounds as described above.

DETAILED DESCRIPTION OF THE INVENTION

The present invention provides DAD isosteres with benzamide, sulfonamide and anthranilamide subunits. The compounds are antiretroviral protease inhibitors. In particular, the compounds inhibit the protease of HIV, more specifically the protease of HIV-1 and HIV-2. The compounds are characteristically different from currently available antiretroviral protease inhibitors. Such differences include, among others, resistance to mammalian and viral protease degradation, which is believed to be due to structural differences, namely the novel, nonpeptidic and achiral benzamide, sulfonamide and anthranilamide subunits that have been introduced into the DAD isosteres. Such differences, such as resistance to-protease degradation, result in improved plasma half-life and oral bioavailability.

The compounds provided by the present invention have the formula:

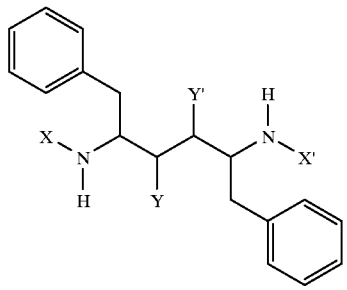

wherein the stereochemistry of each of the benzyl groups on the carbon atoms adjacent to the carbon atoms with the Y and Y' substituents is R or S. Y and Y' are the same or different and are R-hydroxyl, S-hydroxyl, R-amino, S-amino or hydrogen. X and X' are the same or different and are

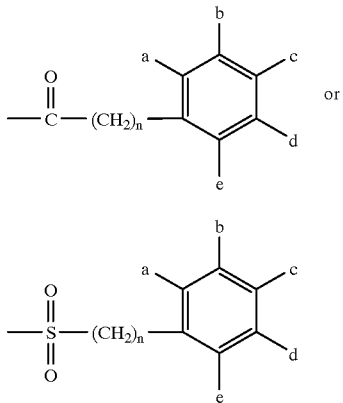

wherein n is 0 or 1. a-e are the same or different and are hydrogen, hydroxyl, halogen, sulfhydryl, carboxyl, carboxamido, a substituted or unsubstituted amino, OR''', a $C_{1-6}$ substituted or unsubstituted straight or branched chain alkyl, a $(CH_2)_mZ''$, an $O(CH_2)_mZ''$, or an $N(R)$ $(CH_2)_mZ''$. The substituent on the substituted amino is $SO_2(CH_2)_pR''$, $CO(CH_2)_pR''$, $COO(CH_2)_pR''$, $CONR_1(CH_2)_pR''$, wherein p=0–20. $R_1$ is a $C_{1-4}$ substituted or unsubstituted straight or branched chain alkyl, wherein the substituent on the substituted $C_{1-4}$ alkyl is hydroxyl, amino, carboxyl or carboxamido, and R'' is hydrogen, hydroxyl, halogen, amino carboxyl, carboxamido, phenyl, pyridinyl, morpholinyl, piperazinyl, indolyl, quinolinyl, isoquinolinyl, thiazolyl, benzimidazolyl, aminothiazolyl, piperidinyl, oxazolyl, cyclopentane, cyclohexane or a $C_{1-20}$ substituted or unsubstituted straight or branched chain alkyl, wherein the substituent on the substituted $C_{1-20}$ alkyl is hydroxyl, amino, carboxyl, phenyl, pyridinyl, carboxamido or OR'. R' is a $C_{1-6}$ substituted or unsubstituted straight or branched chain alkyl, wherein the substituent on the substituted $C_{1-6}$ alkyl is hydroxyl, amino, carboxyl or carboxamido. R''' is a $C_{1-6}$ substituted or unsubstituted straight or branched chain alkyl, wherein the substituent on the substituted $C_{1-6}$ alkyl is hydroxyl, amino, carboxyl or carboxamido, a $(CH_2)_qZ'$, an $O(CH_2)_qZ'$, or an $N(R)$ $(CH_2)_qZ'$, wherein q is an integer of 0 to 4, R is hydrogen or a $C_{1-4}$ substituted or unsubstituted straight or branched chain alkyl, wherein the substituent on the substituted $C_{1-4}$ alkyl is hydroxyl, amino, carboxyl or carboxamido, and Z' is phenyl, pyridinyl, morpholinyl, piperazinyl, indolyl, quinolinyl, isoquinolinyl, thiazolyl, benzimidazolyl, aminothiazolyl, piperidinyl, cyclopentane, cyclohexane or oxazolyl. The substituent on the substituted $C_{1-6}$ alkyl at a-e is hydroxyl, amino, carboxyl, carboxamido, or OR''''. R'''' is a $C_{1-6}$ substituted or unsubstituted straight or branched chain alkyl, wherein the substituent on the substituted $C_{1-6}$ alkyl is hydroxyl, amino, carboxyl or carboxamido. For $(CH_2)_nZ''$, $O(CH_2)_nZ''$, and $N(R)$ $(CH_2)_nZ''$, n=0–4, R is hydrogen or a $C_{1-4}$ substituted or unsubstituted straight or branched chain alkyl, wherein the substituent on the substituted $C_{1-4}$ alkyl is hydroxyl, amino, carboxyl, or carboxamido, and Z'' is phenyl, pyridinyl, morpholinyl, piperazinyl, indolyl, quinolinyl, isoquinolinyl, thiazolyl, benzimidazolyl, aminothiazolyl, piperidinyl, cyclopentane, cyclohexane or oxazolyl. For example, pyridinyl can be 2-,3- or 4-pyridinyl, morpholinyl can be 4-morpholinyl, indolyl can be 2-indolyl, quinolinyl can be 2-quinolinyl, isoquinolinyl can be 1,2,3,4-tetrahydroisoquinolin-2-yl, thiazolyl can be 2- or 4-thiazoly, benzimidazolyl can be 2-benzimidazolyl, and aminothiazolyl can be 2-aminothiazol-4-yl. The ring substituted with a-e can contain a nitrogen and, when the ring does contain a nitrogen, the substituent a, b, c, d or e at the position of the nitrogen does not exist.

Preferred compounds include the compound of the above formula, wherein X and X' are the same, n is 0, Y is R-hydroxyl, Y' is S-hydroxyl, and a and c-e are hydrogen and b is hydroxyl, or a, d and e are hydrogen and b and c are hydroxyl, or a, c and e are hydrogen and b and d are hydroxyl, or a, c and e are hydrogen, b is hydroxyl and d is methyl, or a, c and d are hydrogen, b is hydroxyl and e is methyl, or a, d and e are hydrogen, b is hydroxyl and c is methyl, or a and c-e are hydrogen and b is amino. Also preferred is a compound of the above formula, wherein X and X' are the same, n is 0, Y is S-hydroxyl, Y' is hydrogen, a and c-e are hydrogen, and b is amino or hydroxyl. Another preferred compound is a compound of the above formula, wherein Y is R-hydroxyl, Y' is S-hydroxyl, n is 0, and X and X' are different, wherein, on X, b-e are hydrogen, and a is $N(H)C(O)(O)CH_2$-2-pyridinyl, and on X', a and c-e are hydrogen and b is hydroxyl.

An especially preferred compound is a compound of formula:

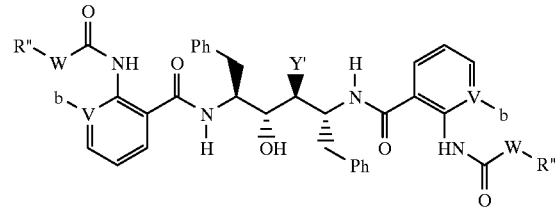

wherein V is carbon or nitrogen, and W is oxygen, nitrogen, $(CH_2)_r$, wherein r=0–20, or a single covalent bond. Preferred compounds of this formula include compounds in which Y is R-hydroxyl, Y' is S-hydroxyl, b is hydrogen, methyl, chloro or hydroxyl, W is oxygen and R'' is $CH_2$-phenyl. Other preferred compounds of this formula include compounds in which Y is R-hydroxyl, Y' is S-hydroxyl, b is hydrogen, V is carbon, W is oxygen or $H_2$ or does not exist, and R" is methyl, ethyl, hydroxyl or $CH_2$-2-pyridinyl.

An especially preferred compound is [2S,3R,4S,5S]-2,5-bis[((N-[N-(2-pyridinylmethyloxy)carbonyl]anthranyl) amino]-3,4-dihydroxy-1,6-diphenylhexane. Also referred are compounds of this formula, wherein Y is S-hydroxyl, Y' is hydrogen, b is hydrogen, V is carbon, W is oxygen, and R" is selected from the group consisting of $CH_2$-phenyl and $CH_2$-2-pyridinyl. An especially preferred compound is [2S, 3S,5S]-2,5-bis[((N-[N-(2-pyridinylmethyloxy) carbonyl] anthranyl)amino]-3-hydroxy-1,6-diphenylhexane.

Accordingly, the present invention provides symmetric and asymmetric 2,5-diamino-3,4-disubstituted-1,6-diphenylhexane (DAD) isosteres comprising benzamide, sulfonamide, and anthranilamide subunits. The asymmetric compounds can be asymmetric with respect to X and X' or with respect to the substituents a-e that are present on X and X', in particular with respect to substituted amino groups, for example. Representative compounds are presented in Tables I–V. The substituents on these compounds, in particular on the substituted amino groups, may be further modified as necessary to affect activity and ease the preparation of a given pharmaceutical formulation, for example.

The compounds of the present invention may be synthesized by methods known to those of skill in the art. For example, DAD (Kempf et al., *J. Org. Chem.*, 57, 5692–5700 (1992); Stuk et al., *J. Org. Chem.*, 59, 4040–4041 (1994)) can be reacted with suitably substituted acid or acid chloride in methylene chloride, toluene, preferably dimethylformamide at ambient temperature, i.e., room temperature. The acids also can be condensed with DAD using standard peptide coupling agents (Bodanszky et al., *In The Practice of Peptide Synthesis*, Springer-Verlag, New York, N.Y. (1984)). Suitable methods of synthesis are described in Examples 1–4. The asymmetric compounds of the present invention also may be synthesized in accordance with the present inventive method as described in Examples 5–6 and in Schemes V–VIII. The sulfonamides are prepared by reaction of a suitably substituted benzene sulfonic acid with DAD/Boc-DAD or other such intermediates, such as those used in the synthesis of Diol-10, Diol-48, DD-5, ND-4 and DN-11. Alternatively sulfonamides are prepared by the reaction of a suitably substituted nitro benzene sulfonyl chloride with the above intermediates. The nitro substituent is manipulated to provide the desired amino analogs, which in turn can be protected, i.e., acetylated, alkylated or converted into hydroxyl or other such derivative by standard procedures as needed.

Also provided by the present invention is a pharmaceutical composition comprising a retroviral proliferation-inhibiting, particularly a HIV proliferation-inhibiting and more particularly a HIV-1 and/or HIV-2 proliferation-inhibiting, effective amount of one or more of a compound as described above, alone or in combination with one or more of a currently available anti-retroviral compound, such as AZT, ddI, ddC, D4T, lamivudine or 3TC, in a pharmaceutically acceptable carrier. Pharmaceutically acceptable carriers are well-known to those who are skilled in the art. The choice of carrier will be determined in part by the particular composition, as well as by the particular method used to administer the composition. Accordingly, there is a wide variety of suitable formulations of the pharmaceutical composition of the present invention.

Formulations suitable for oral administration can consist of (a) liquid solutions, such as an effective amount of the polymer-bound composition dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

Accordingly, the present invention also provides a method of treating a retroviral, particularly a HIV infection and more particularly a HIV-1 or HIV-2 infection, in a mammal, particularly a human, wherein a retroviral proliferation-inhibiting amount of one or more of the present inventive compounds, alone or in combination with one or more other antiretroviral therapies or compounds, such as AZT, ddI, ddC, D4T, lamivudine or 3TC, is administered to a mammal infected with a retrovirus, particularly HIV and more particularly HIV-1 or HIV-2, the proliferation of which is inhibited by a retroviral proliferation-inhibiting amount of a present inventive compound. The dose administered to an animal, particularly a human, in the context of the present invention should be sufficient to effect a therapeutic response in the animal over a reasonable time frame. The dose will be determined by the strength of the particular composition employed and the condition of the animal, as well as the body weight of the animal to be treated. The size of the dose also will be determined by the existence, nature, and extent of any adverse side-effects that might accompany the administration of a particular composition. What constitutes a retroviral proliferation-inhibiting amount, particularly a HIV proliferation-inhibiting amount, and more particularly a HIV-1 or HIV-2 proliferation-inhibiting amount, of one or more compounds of the present invention, alone or in combination with one or more other currently available antiretroviral compounds can be determined, in part, by use of one or more of the assays described herein. Similarly, whether or not a given retrovirus is inhibited by a retroviral proliferation-inhibiting amount of a compound of the present invention can be determined through the use of one or more of the assays described herein or in the scientific literature or as known to one of ordinary skill in the art.

One skilled in the art will appreciate that suitable methods of administering the compounds and pharmaceutical compositions of the present invention to an animal are available, and, although more than one route can be used to administer a particular composition, a particular route can provide a more immediate and more effective reaction than another route. One or more of the present inventive compounds, alone or in combination with one or more other antiretroviral therapies or compounds, can be administered to a mammal, in particular a human, as a prophylactic method to prevent retroviral, particularly HIV and more particularly HIV-1 or HIV-2, infection.

Also provided by the present invention is a method of synthesizing the asymmetric compounds of the present invention. For example, a solution of benzyloxycarbonyl chloride, preferably 1M, in $CH_2Cl_2$, is added slowly, preferably at a rate of 1 ml/min, to a solution of DAD in a solvent, preferably methylene chloride (preferred ratio of 1 g:500 ml), containing a base, preferably diisopropyl ethylamine or triethylamine. The resulting product is filtered to remove insolubles, washed successively with 1% $KHSO_4$ brine and dried, preferably over anhydrous $K_2CO_3$, to provide monobenzyloxycarbonyl protected DAD (MZ-DAD). MZ-DAD can then be manipulated using standard reactions to provide asymmetric inhibitors. The synthesis of asymmetric compounds of the present invention is described in Schemes V–VIII, and also in Examples 5 and 6. The synthesis of symmetric compounds of the present invention is described in Scheme I.

In addition, compounds of the present invention, such as diol-38 (Table IV, compound 27) and diol-48 (Table IV, compound 34), demonstrate good fluorescence. The determination of which compounds of the present invention fluoresce can be done in accordance with methods well-known to those of ordinary skill in the art. Such fluorescence can be used to assay for antiviral activity of newly discovered compounds. For example, a fluorescent compound of the present invention can be used as a standard in an antiviral activity assay. The fluorescence of the compound can be measured in the absence and presence of a viral enzyme, such as a retroviral enzyme, in particular a retroviral protease, e.g., an HIV protease, in vitro. A test compound can then be added to the test system comprising the fluorescent compound and the enzyme. The decreased fluorescence of the fluorescent compound of the present invention in the absence and presence of the test compound can be measured and quantitated as a measure of the antiviral activity of the test compound.

The following examples further illustrate the present invention, but do not limit the scope thereof.

EXAMPLE 1

This example describes the synthesis of DAD isosteres with benzamide and anthranilamide subunits.

Compounds 5–36 were synthesized as shown in Scheme I. The inhibitor core unit 3 (2S,3R,4S,5S-2,5-diamino-1,6-diphenyl-3,4-hexanediol) was synthesized by McMurray coupling of natural Boc-phenylalaninal (Kempf et al. (1992), supra). The 2,5-diamino compound 3 (X=OH) was condensed with suitably substituted benzoic acid using the 1-H-benzatriol-1-yl-1,1,3,3-tetramethyl-ammonium tetrafluoroborate (TBTU)/1-hydroxybenzotriazole (HOBt)/ diisopropylethyl amine (DIPEA) method to provide compounds 7–22. The 2,5-diamino compound 3 (where, in Scheme I, X=OH) was condensed with suitably substituted N-acyl anthranilic acid using the TBTU/HOBt/DIPEA method to provide compounds 26–34. The N-acyl anthranilamides were prepared by reaction of anthranilic acid with corresponding acid chloride. Compound 29 was prepared by hydrogenolysis of a compound wherein $R_2$ was $OCH_2$-phenyl. Deshydroxy compounds were prepared from compound 4 (Kempf et al. (1993), supra). The condensation of the 2,5-diamino compound 3 with suitably substituted phenylacetic acid using this procedure provided compounds 5a and 5b. The ethers 18a and 19a were prepared by the reaction of methyl-3-hydroxybenzoate with corresponding halides in the presence of NaH according to Scheme II. 3-hydroxy-5-methylbenzoic acid (14a) was prepared from sodium acetopyruvate according to Scheme III (Turner et al., *J. Org. Chem.*, 24, 1952 (1959)). 2-methyl-5-hydroxybenzoic acid (15a) was prepared by a Diels-Alder condensation of 2-methylfuran and ethyl propiolate in the presence of an aluminum chloride according to Scheme IV (McCulloch et al., *Can J. Chem.*, 49, 3152 (1971)). The deshydroxy compounds 24 and 25 were prepared by condensation of 2S,3S,5S-2,5-diamino-1,6-diphenyl-3-hexanol (4, X=H; Kempf et al., *Recent Advances in the Chemistry of Anti-Infective Agents*, Royal Society of Chemistry, Bently et al., eds., pp. 297–313 (1993)) with suitably substituted benzoic acid using the TBTU/HOBt/DIPEA method (Scheme I, X=H). The structures of all compounds thus prepared were established by proton nuclear magnetic resonance ($^1H$ NMR) spectroscopy and mass spectral (FAB and/or high resolution mass spectra (HRMS)) analysis. $^1H$ NMR spectra were recorded on a Varian XL-200 and 500 MHz spectrometer; data were reported in δ ppm scale relative to TMS. FAB spectra and HRMS were recorded on a VG ZAB-2F spectrometer (Manchester, England) and on a VG70-250 spectrometer, respectively.

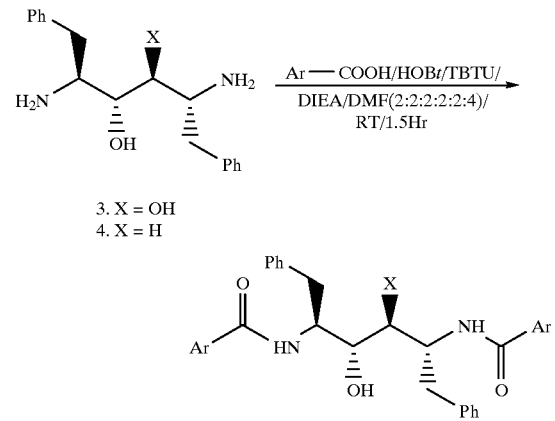

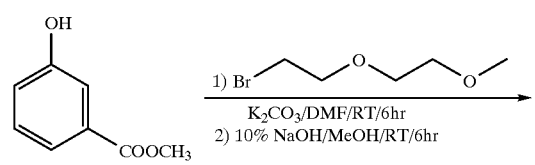

11
-continued
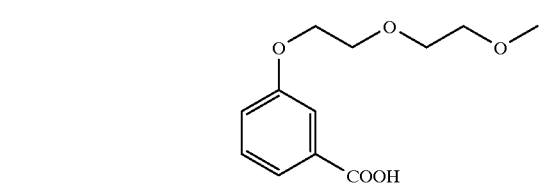
18a
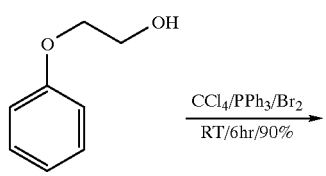
CCl₄/PPh₃/Br₂
─────────────
RT/6hr/90%
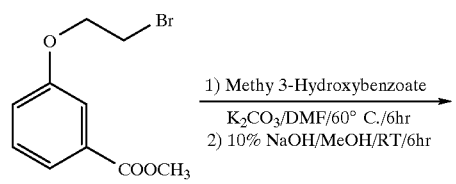
1) Methy 3-Hydroxybenzoate
K₂CO₃/DMF/60° C./6hr
─────────────────────
2) 10% NaOH/MeOH/RT/6hr
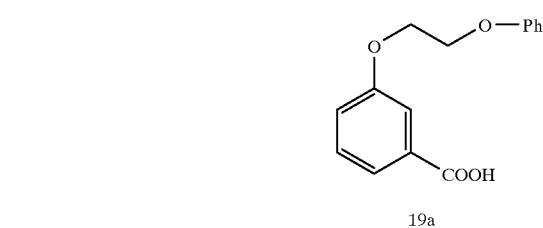
19a
Scheme III
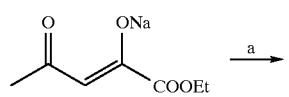
12
-continued
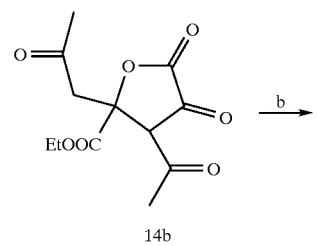
14b
a) acetic acid:water (1:1)/2hr/RT. b) MgO/waterΔ/30min.
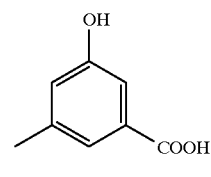
14a
Scheme IV
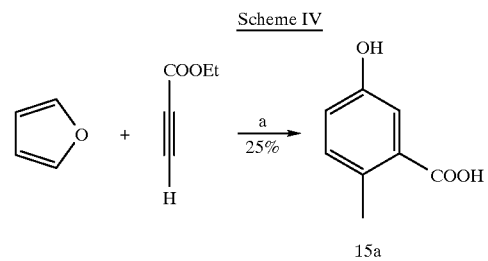
15a
a) AlCl₃(3eq.)/CH₂Cl₂/30min.
SCHEME V
ASYMMETRIC COMPOUNDS: GENERAL SCHEME FOR SYNTHESIS OF DN SERIES
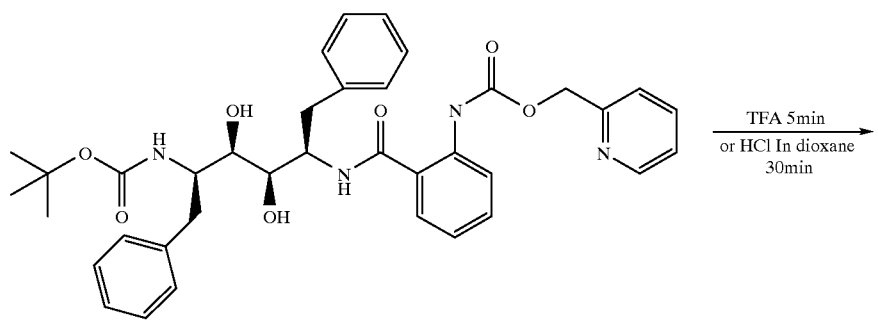
TFA 5min
or HCl In dioxane
30min -continued
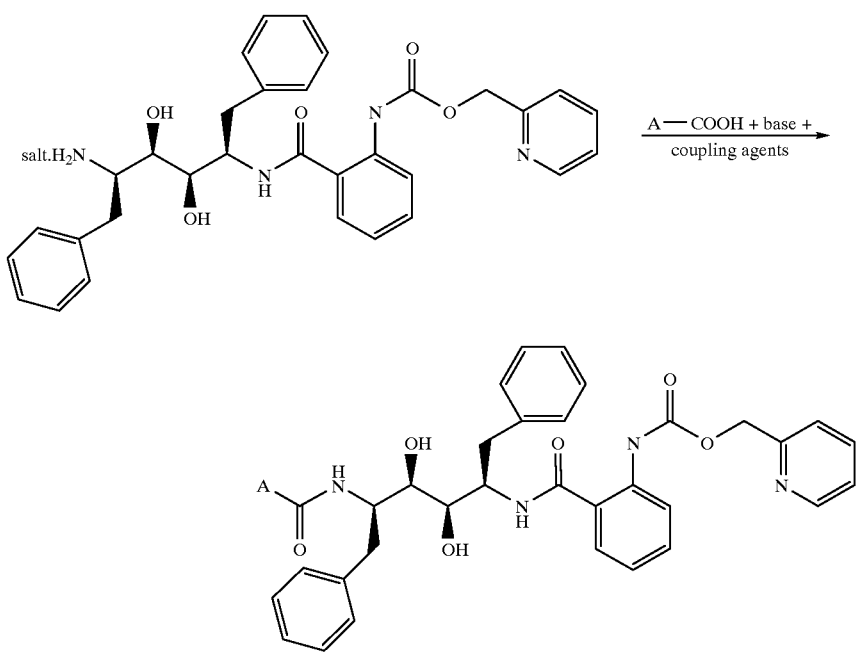
SCHEME VI
ASYMMETRIC COMPOUNDS: GENERAL SCHEME FOR SYNTHESIS OF ND SERIES
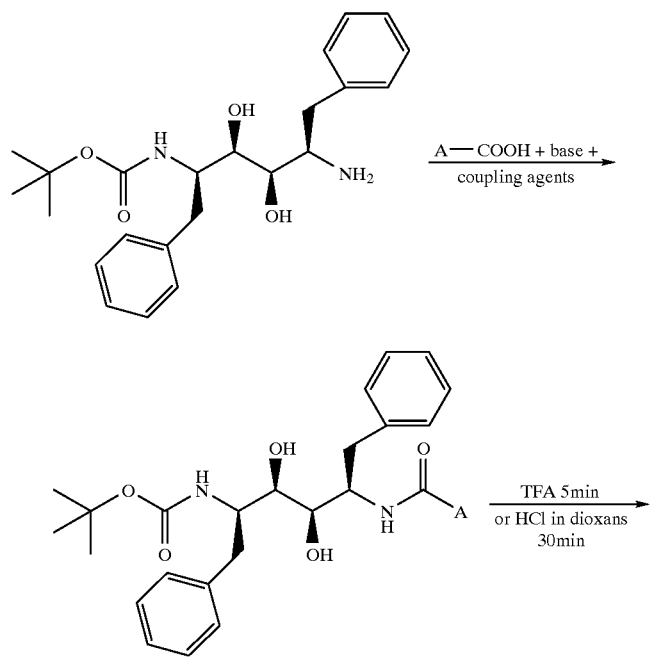

-continued
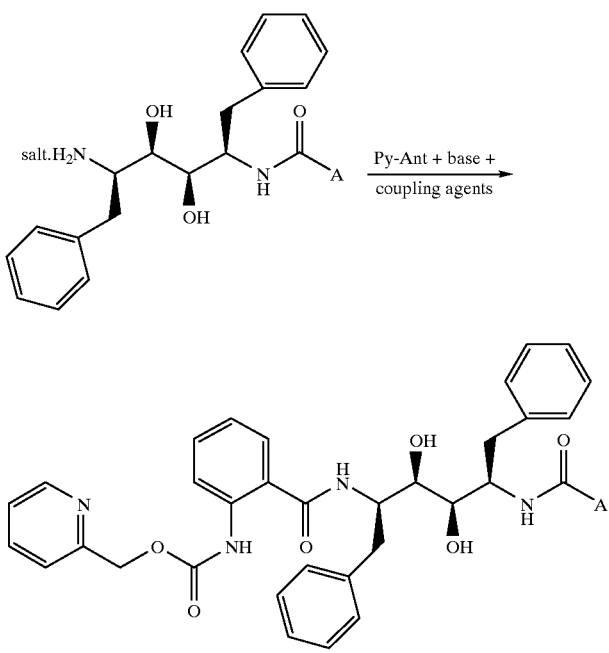
ND-4 when A is 3-hydroxyphenyl
SCHEME VII
ASYMMETRIC COMPOUNDS: GENERAL SYNTHETIC SCHEME FOR DESHYDROXY COMPOUNDS
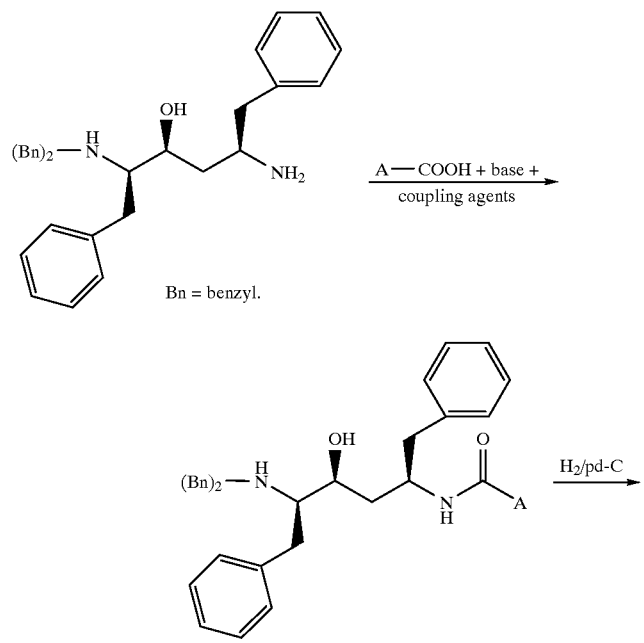
Bn = benzyl.

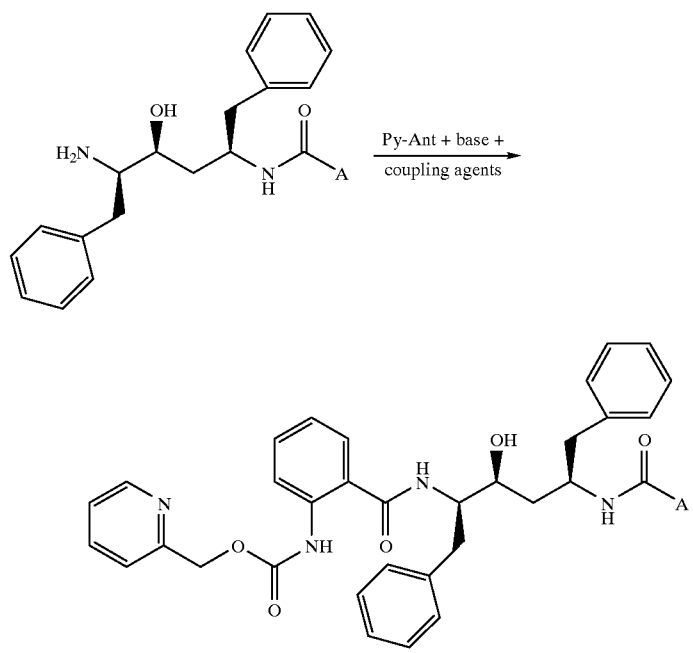
SCHEME VIII
ASYMMETRIC COMPOUNDS: GENERAL SYNTHETIC SCHEME FOR DESHYDROXY COMPOUND
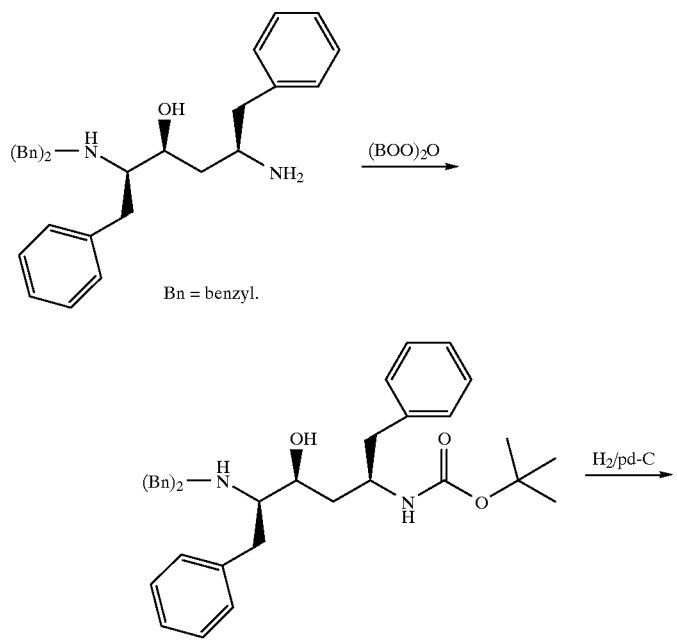
Bn = benzyl.

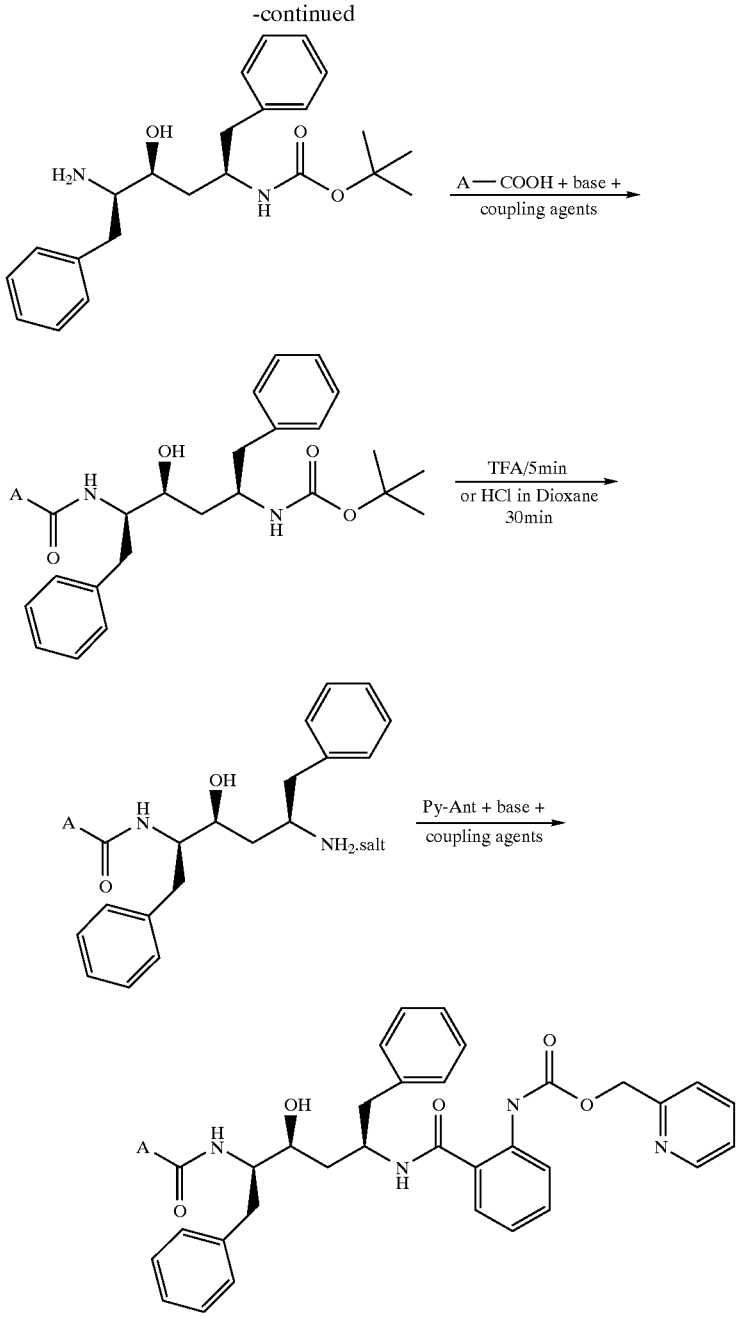

Bisamides, such as (2S,3R,4S,5S)-2,5-bis[((3-hydroxyphenyl)carbonyl)amino]-3,4-dihydroxy-1,6-diphenylhexane (7), were prepared as follows. A solution of 60 mg (0.43 mmol) of 3-hydroxy-benzoic acid, 122 mg (0.38 mmol) of TBTU, 59 mg (0.43 mmol) of HOBT, 174 μl of DIPEA, and 100 mg (0.19 mmol) of 2S,3R,4S,5S-2,5-diamino-3,4-dihydroxy-1,6-diphenyl-hexane (Kempf et al., J. Org. Chem., 57, 5692 (1992)) in 4 ml of dimethylformamide (DMF) was stirred at room temperature for 1.5 h, after which the reaction was quenched with a drop of 4-(2-aminoethyl)-morpholine. The solvent and volatiles were removed under reduced pressure, and the residue was taken up in ethyl acetate and washed sequentially with 10% $KHSO_4$, water, and aqueous $NaHCO_3$, brine-dried and concentrated in vacuo. Crude product was crystallized from methanol:water (1:10) as a white solid, yielding 80 mg (78%) (MS(FAB) m/z 541 (M+); $^1H$ NMR: δ).

2-methyl-5-hydroxybenzoic acid (15a; Scheme III) was prepared as follows. A solution of 2-methylfuran (6.56 g) in $CH_2Cl_2$ (120 ml) was added, at about 20° C. to a mixture of ethyl propiolate (7.84 g) and anhydrous $AlCl_3$ (10.64 g) in $CH_2Cl_2$. The reaction mixture was allowed to stand at room temperature for 30 min with occasional shaking and was then shaken vigorously with cold water. The organic layer was extracted with 5% NaOH solution (3×10 ml), and the combined aqueous layer was acidified and extracted with ethyl acetate (3×20 ml). The combined organic layer was washed with water, brine-dried and partitioned with aqueous $NaHCO_3$ (3×10 ml). The bicarbonate-soluble fraction, after reacidification and extraction with ether, gave 15a (1.9 g) as a colorless solid; mp 181–183° (lit 185°) (McCulloch (1971), supra). $^1$H NMR (CD$_3$OD): δ2.48 (s,3H), 6.88 (dd, J$_1$=3 Hz, J$_2$=8.2 Hz, 1H), 7.09 (d, J=8 Hz, 1H) and 7.36 (d, J=2.8 Hz, 1H).

3-hydroxy-5-methyl-benzoic acid (14a, Scheme II) was prepared as follows. A mixture of 321 g (1.78 mol) of ethyl sodiumacetopyruvate (Marvel et al., *Org. Syn.* 1944 *Coll.*, I, 238 (1944)), 400 ml acetic acid, and 400 ml water was stirred for 2 h. During this time, the solid was dissolved and the solution became gray. The content of the flask was poured onto 1 kg of crushed ice and 150 ml of sulfuric acid. The resulting solid was separated by filtration, washed with cold water, and dried to afford γ-lactone 14b (Scheme III, 195 g (86%), mp 89–90° C.). The γ-lactone 14b (200 g, 695 mmol) and MgO (120 g, 3 mol) were added with stirring to 1.5 l of water, previously warmed on a steam bath. The reaction mixture became deep reddish orange in color and turned light brown in about 15 min. Stirring was continued on a steam bath for an additional 30 min after the complete addition of solid. The magnesium oxalate and excess MgO were removed by filtration and washed with warm water. The filtrate was concentrated in vacuo to 200 ml, placed in an ice bath and acidified with dilute HCl to provide 3-hydroxy-5-methylbenzoic acid 14a (27 g (28%), recrystallized from ether, mp 205–207° C. (lit. 207–208° C.) (Turner et al. (1959), supra), $^1$H NMR (CDCl$_3$): 0.32. (s,3H), 6.8 (m, 1H), 7.2 (m, 2H), 8.7 (m, 1H)).

3-[2-((methoxy)ethoxy)ethoxy]benzoic acid (18a, Scheme II) was prepared as follows. A mixture of 240 mg (1.6 mmol) of methyl-3-hydroxybenzoate, 200 mg of anhydrous K$_2$CO$_3$ and 0.27 ml (2 mmol) of 1-bromo-2(2-methoxyethoxy)ethane in DMF was heated with stirring at 50° C. for 6 h. Then, the DMF was evaporated under reduced pressure and the residue was extracted with ether. Methanol (5 ml) and NaOH (2 ml) were added to the methyl benzoate and stirred at room temperature for 4 h. The methanol was removed under reduced pressure, washed with ether (5 ml), acidified and extracted with ethyl acetate (3×10 ml). The combined ethyl acetate layer was washed with brine, dried and evaporated to provide 18a (310 mg, 79%) as a thick liquid; $^1$H NMR (CDCl$_3$): 3.4 (s, 3H), 3.5 (M, 2H), 3.7 (m, 2H), 3.9 (m, 2H), 4.2 (m, 2H), 7.16 (m, 1H), 7.36 (m, 1H), 7.62 (m, 1H) and 7.69 (m, 1H).

3-[2-(phenoxy)ethoxy]benzoic acid (19a, Scheme II) was prepared as follows. To a stirred and cooled solution of triphenyl phosphene (1.9 g, 7.2 mmol) in anhydrous methylene chloride (5 ml), under argon, a solution of bromine (0.7 ml) in CCl$_4$ (2 ml) was added slowly during 15 min. The stirring was continued for 30 min, after which 20 phenoxyethanol (1 g, 7.2 mmol) in CH$_2$Cl$_2$ (2 ml) was added slowly. The reaction mixture was allowed to warm to room temperature and left overnight. The excess of solvents were stripped off and the residue was repeatedly extracted with petroleum ether. Evaporation of petroleum ether gave 2-phenoxyethyl bromide (1.4 g, 95%); $^1$H NMR (CDCl$_3$): 3.66 (m, 2H), 4.30 (m, 2H) and 6.9–7.4 (m, 5H).

2-phenoxyethyl bromide was converted to 3-[2-(phenoxy) ethoxy]benzoic acid (19b) by following an analogous procedure as described for compound 18a; (M+H)$^{+1}$=258; $^1$H NMR (CDCl$_3$): δ 4.3 (m, 4H), 6.9–7.0 (m, 6H), 7.2–7.5 (m, 3H) and 12.5 (s, 1H).

EXAMPLE 2

This example describes the synthesis of [2S,3R,4S,5S]-2,5-bis[((N-[N-(2-pyridinylmethyloxy)carbonyl ]anthranyl)amino]-3,4-dihydroxy-1,6-diphenylhexane (Diol-48).

Diol-48 (compound 34) was synthesized according to the following reaction scheme:

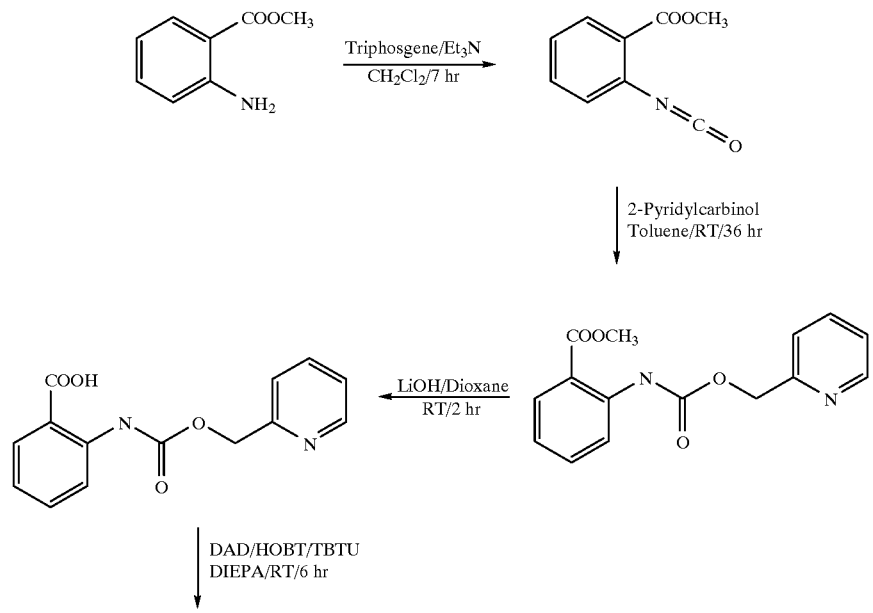

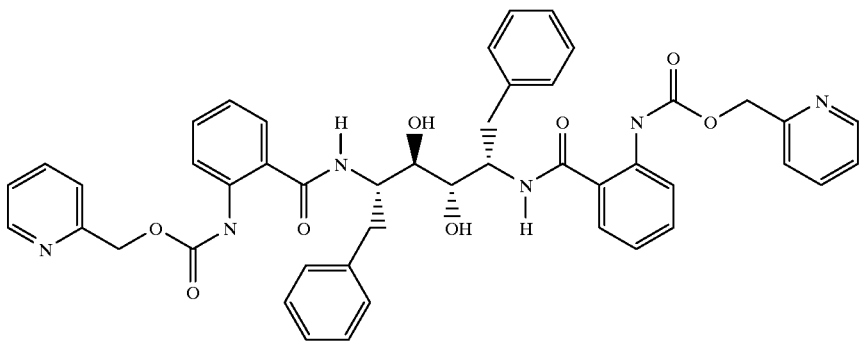

A solution of methyl anthranilate (9.06 g, 60 mmol) in methylene chloride (100 ml) containing triethylamine (11 ml) was added slowly (at a rate of 2 ml/min) to a stirred solution of triphosgene in methylene chloride (250 ml) (Pavel et al., J. Org. Chem., 59, 1937–1938 (1994)). After complete addition, the stirring was continued for an additional 2 hr and volatiles were removed by evaporation under reduced pressure. The salts were separated by dissolving the reaction mixture in anhydrous ether followed by filtration under anhydrous conditions. The resulting isocyanate was used in the next step without further purification.

A solution of methyl anthranilate isocyanate (1 g, 5.64 mmol) and 2-pyridinylcarbinol (0.616 g, 0.545 ml, 5.64 mmol) in 40 ml of toluene was stirred at room temperature under $N_2$ atmosphere for 36 hr. The solvent was removed under vacuum, and the residue was purified by ilica gel chromatography using the solvent system EtOAc-hexanes 1:1, to give 0.72 g (45%) of the carbamate. MS(M+H)=287; $^1$H NMR (DMSO-$d_6$), δ 3.85 (s, 3H), 5.25 (s, 2H), 7.1 (m, 1H), 7.3–7.4 (m, 2H), 7.6 (m, 1H), 7.8–7.9 (m, 2H), 8.1 (m, 1H), 8.58 (m, 1H), 10.4 (s, 1H).

The resulting product was dissolved in dioxane (15 ml) and saponified with lithium hydroxide (19 ml, 1N) at room temperature for 2 hr. The volatiles were removed, and the residue was acidified to pH 5.5 and extracted with ethyl acetate. Evaporation of the organic layer provided (N-2-pyridinylmethyloxycarbonyl)-anthranilic acid (Py-Ant).

A solution of methyl N[2-pyridinylmethoxy)carbonyl] anthranilic acid (56.5 mg, 0.2 mmol), DAD (30 mg, 0.1 mmol), HOBT (31 mg, 0.2 mmol), TBTU (65 mg, 0.2 mmmol), and DIPEA (52 mg, 70 μl, 0.4 mmol) in DMF (10 ml) was stirred at room temperature for 6 hr. The solvents were removed under vacuum, and the residue was diluted with ethyl acetate, washed sequentially with a solution of $KHSO_4$ (pH=5), water, and aqueous $NaHCO_3$, and dried over $MgSO_4$. The yield was 54 mg of crude product. MS (M+H)=809; $^1$H NMR (DMSO-$d_6$), δ 6 2.80–2.85 (m, 1H), 2.89–2.93 (m, 1H), 2.94–3.01(m, 2H), 3.59–3.66 (m, 2H), 4.57–4.67 (m, 2H), 5.10–5.20 (m, 5H), 5.44(d, J=3.2Hz, 1H), 7.25–7.46 (m, 18H), 7.73–7.81(m, 4H), 8.09–8.12 (m, 2H), 8.32 (d, J=3.6 Hz, 1H), 8.49 (d, J=3.6 Hz, 1H), 8.54 (m, 2H), 10.60 (s, 1H), 10.76 (s, 1H). $K_i$=64 pM.

EXAMPLE 3

This example describes the synthesis of Diols 43, 39B, 38, 42, 36 and 45.

Diol-43 (compound 32, Table IV) was prepared following a procedure similar to that described for Diol-48 (compound 34, Table IV), using 1.1 molar equivalent of 3-chloro-N-((benzyloxy)carbonyl)-anthranilic acid instead of N-((2-Pyridinylmethyloxy)carbonyl)-anthranilic acid.

Diol-39B (compound 29, Table IV) was prepared following a procedure similar to that described for Diol-48 (compound 34, Table IV) using 1.1 molar equivalent of [N-((2-benzyloxy)methyl)carbonyl]-anthranilic acid instead of N-((2-Pyridinylmethyloxy)carbonyl)-anthranilic acid. The intermediate Diol-39, a compound like compound 29 with the exception that the $R_2$ group is $OCH_2$-phenyl, thus obtained was debenzylated by hydrogenation with 10% Pd on carbon to provide Diol-39B. $C_{36}H_{38}N_4O_8$; MW=654; MS (M+Na)+=677; $^1$H NMR (methanol-$d_4$), δ 2.82–2.98 (m, 2H), 3.03–3.11 (m, 4H), 3.73 (s, 2H), 3.85 (m, 1H), 3.94–4.01 (m, 5H), 4.65–4.75 (m, 2H), 7.08–7.51 (m, 18H), 8.31 (d, J=8 Hz, 2H).

Diol-42 (compound 31, Table IV) was prepared following a procedure similar to that described for Diol-48 (compound 34, Table IV), using 1.1 molar equivalent of 3-methyl-N-((benzyloxy)carbonyl)-anthranilic acid instead of N-((2-Pyridinylmethyloxy)carbonyl)-anthranilic acid. $C_{50}H_{50}N_4O_8$; MW=834; MS (M+Na)+=856; $^1$H NMR ($CDCl_3$ δ 2.15 (m, 6H), 2.85–2.89 (m, 2H), 2.99 (m, 3H), 3.08 (dd, J=5.6; 1.8 Hz,2H), 3.66 (bs, 4H), 4.57–4.64 (m, 2H), 4.96 (m, 2H), 6.9 (m, 1H), 6.96–7.02 (m, 2H), 7.17–7.25 (m, 26H).

Diol-36 (compound 26, Table IV) was prepared following a procedure similar to that described for Diol-48 (compound 34, Table IV), using 1.1 molar equivalent of N-acetyl-anthranilic acid instead of N-((2-Pyridinylmethyloxy) carbonyl)-anthranilic acid. $C_{36}H_{38}N_4O_6$; MS (M+H)+=633; $^1$H NMR (methanol-$d_4$), δ 1.88 (s 3H), 2.01 (s, 3H), 2.83 (m, 1H), 3.03–3.11 (m, 3H), 3.63 (s, 1H), 3.79 (m, 2H), 4.73 (m, 2H), 7.06 (m, 1H), 7.14–7.45 (m, 14H), 7.54 (m, 1H), 8.07 (m, 2H).

Diol-45 (compound 30, Table. IV), was prepared following a procedure similar to that described for Diol-48 (compound 34, Table IV), using 1.1 molar equivalent of 2-(((N-benzyloxy)carbonyl)amino))) nicotinic acid instead of N-((2-Pyridinylmethyloxy)carbonyl)-anthranilic acid. $C_{46}H_{44}N_6O_8$; MS(M+Na)+=831. $^1$H NMR (methanol-$d_4$), δ 2.91 (m, 1H), 3.01–3.20 (m, 3H), 3.5 (m, 2H), 3.9 (m, 2H), 4.6 (m, 2H), 5.0 (m, 4H), 7.1–7.3 (m, 22H), 7.84 (m, 1H), 8.1 (m, 1H), 8.3 (m, 2H).

EXAMPLE 4

This example describes the synthesis of [2S,3S,5S]-2,5-bis [((N-[N-(2-pyridinylmethyloxy)carbonyl]anthranyl) amino]-3-hydroxy-1,6-diphenylhexane (DD-5).

DD-5 (compound 36, Table IV) was synthesized according to the following reaction scheme:

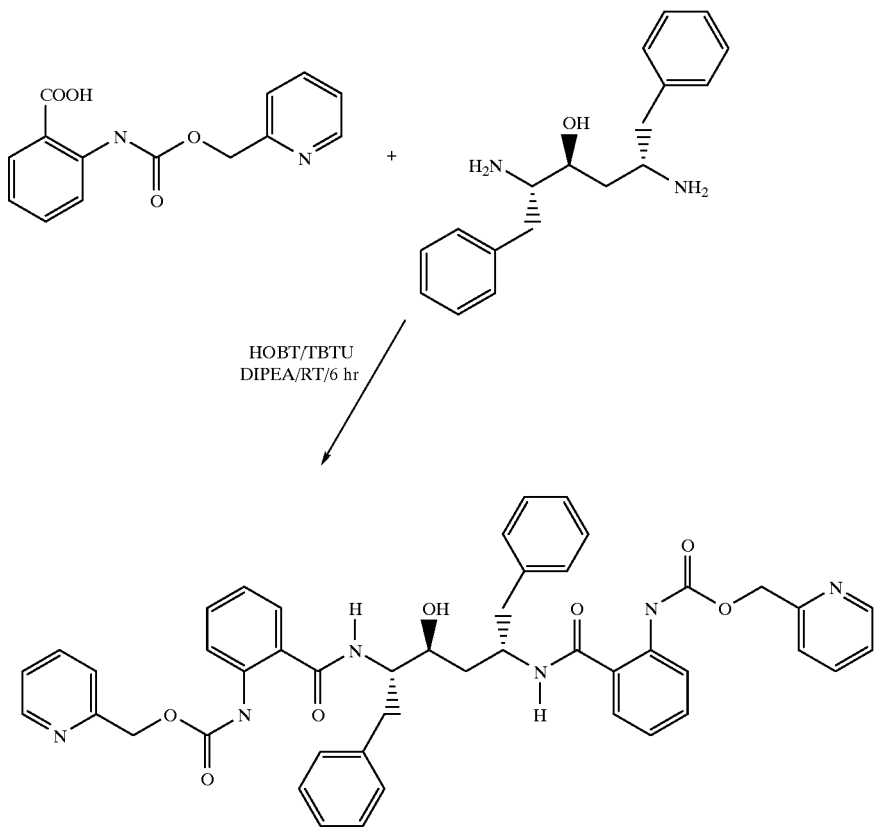

A solution of N-((2-pyridinylmethyloxy)carbonyl)-anthranilic acid (42 mg, 0.15 mmol), (2S,3S,5S)-2,5-bisamino-3-hydroxyl-1,6-diphenylhexane (Stuk et al., *J. Org. Chem.*, 59, 4040 (1994); 20 mg, 0.07 mmol), HOBT (23 mg, 0.21 mmol), TBTU (46 mg, 0.14 mmol), in DMF (10 ml) was treated with DIPEA (37 mg, 49 μl, 0.28 mmol) and then stirred at room temperature for 7 hr. The solvents were removed under vacuum, and the residue was diluted with ethyl acetate, washed sequentially with an aqueous solution of $KHSO_4$ (pH=5), water, and aqueous $NaHCO_3$, and dried over $MgSO_4$. Yield: 31 mg (27%). The compound was crystallized from the solvent system EtOAc-hexanes (1:3). The yield after crystallization was 22 mg. MS $(M+Na)^+=817$; $^1H$ NMR (Methanol-$d_4$), δ 1.77–1.81 (m, 2H), 2.72–2.77 (m, 1H), 2.83–2.86 (m, 2H), 2.91 (d, J=7.7 Hz, 2H), 3.81–3.85 (m, 2H), 4.61–4.70 (m, 2H), 5.19–5.21 (m, 4H), 6.99–7.05 (m, 4H), 7.09–7.13 (m, 4H), 7.19–7.20 (m, 2H), 7.24–7.33 (m, 8H), 7.39–7.44 (m, 6H), 7.68–7.72 (m, 2H), 8.13–8.15 (m, 2H), 8.43–8.45 (m, 2H). $K_i$=74pM.

EXAMPLE 5

This example describes the synthesis of [2S,3R,4S,5S]-2-[N-[tert-butyloxy)carbonyl]amino]-5-[((N-[N-2-pyridinylmethyloxy)carbonyl]anthranyl)amino]-3,4-dihydroxy-1,6-diphenylhexane (DN-11).

DN-11 was synthesized according to the following reaction scheme:

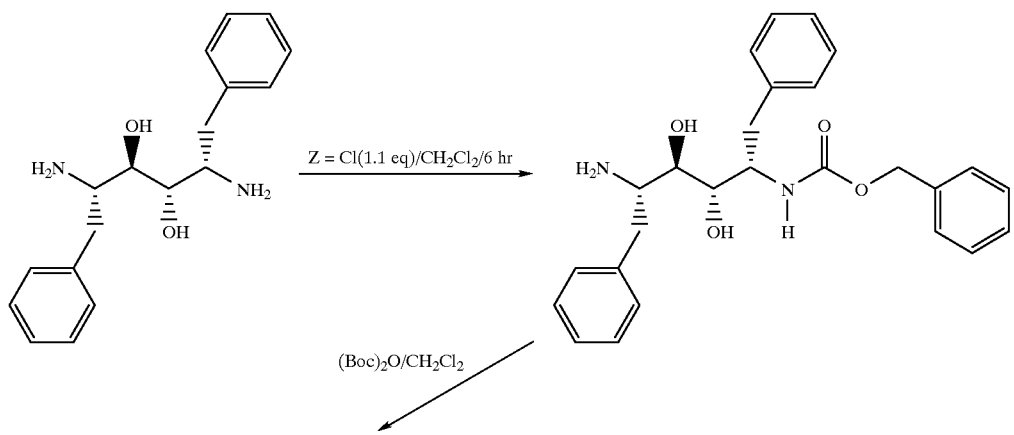

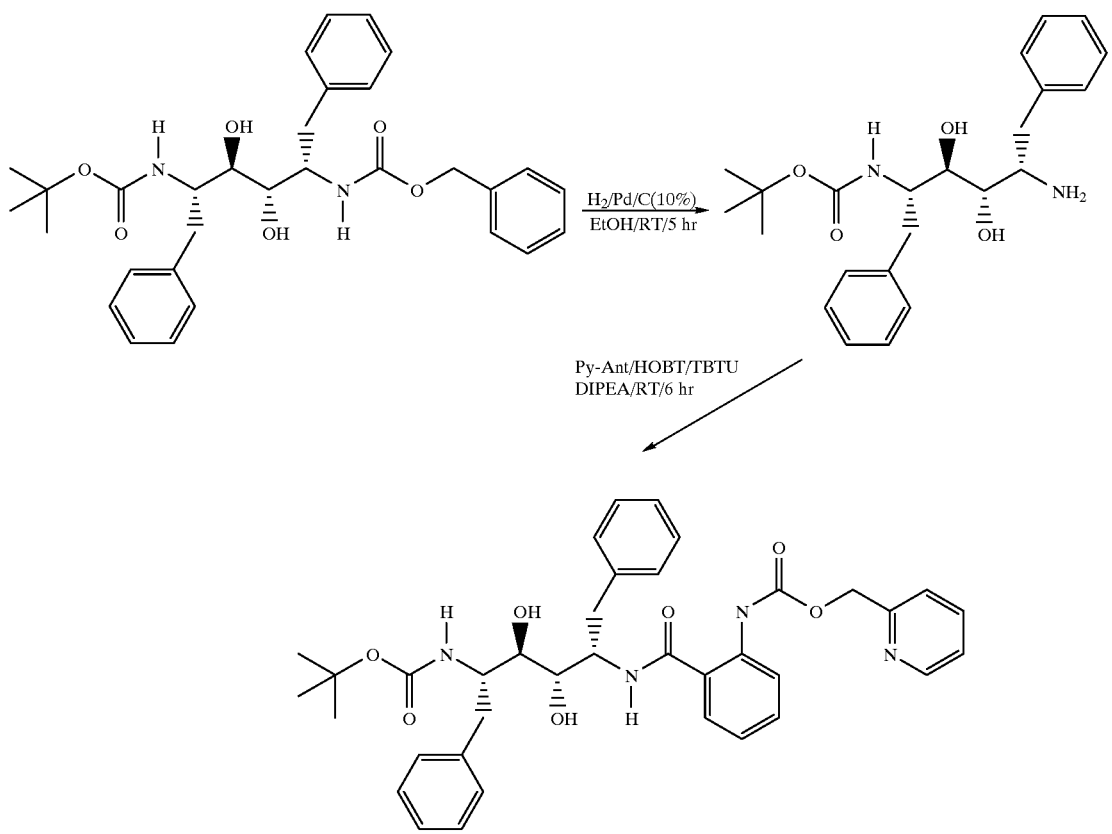

A solution of (2S,3R,4S,5S)-2-amino-5-(N-benzyloxycarbonylamino)-3,4-dihydroxy-1,6-diphenylhexane (250 mg, 0.575 mmol) and (Boc)$_2$O (138 mg, 0.63 mmol) in methylene chloride (15 ml) was stirred at room temperature for 24 hr. The volatiles were removed under vacuum, and the residue was diluted with ethyl acetate, washed sequentially with 10% solution of KHSO$_4$ water, and aqueous NaHCO$_3$, and dried over MgSO$_4$. The yield of product was 308 mg. The compound was crystallized from the solvent system EtOAc-hexanes 1:2. The yield of crystallized product was 270 mg (88%).

A continuous stream of hydrogen was bubbled through a solution of (2S,3R,4S,5S)-2-(N-tert-butyloxycarbonyl amino)-5-(N-benzyloxycarbonylamino)-3,4-dihydroxy-1,6-diphenylhexane (500 mg) in ethanol (80 ml) containing 10% Pd on carbon (40 mg) for 5hr (Bodanszky et al. (1984), supra, at page 153). The reaction mixture was filtered through celite and concentrated in vacuum to provide 316 mg of (2S,3R,4S,5S)-2-(N-tert.-butyloxycarbonylamino)-5-amino-3,4-dihydroxy-1,6-diphenylhexane (Boc-DAD).

A solution of (N-2-pyridinylmethyloxy)carbonyl)-anthranilic acid (Py-Ant, 30 mg, 0.11 mmol), Boc-DAD (40 mg, 0.1 mmol), HOBT (16 mg, 0.1 mmol), TBTU (32 mg, 0.1 mmol), in DMF (20 ml) was treated with DIPEA (26 mg, 35 μl, 0.2 mmol) and then stirred at room temperature for 6 hr. The solvents were removed under vacuum, and the residue was diluted with ethyl acetate, washed sequentially with a 10% solution of KHSO$_4$, water and aqueous NaHCO$_3$, and dried over MgSO$_4$. Yield: 65 mg. The compound was crystallized from the solvent system EtOAc-hexanes (1:1). The yield after crystallization was 26 mg. MS(M+Na) 677; $^1$H NMR (methanol-d$_4$), δ 1.231 (m, 9H), 2.59–2.64 (m, 2H), 2.89–2.93 (m, 1H), 2.97–3.07 (m, 2H), 3.59–3.67 (m, 2H), 4.15–4.19 (m, 1H), 4.66–4.69 (m, 2H), 5.21–5.29 (m, 2H), 7.06–7.09 (m, 1H), 7.11–7.14 (m, 2H), 7.17–7.25 (m, 7H), 7.30–7.32 (m, 2H), 7.35–7.37 (m, 1H), 7.41–7.45 (m, 1H), 7.51–7.54 (m, 2H), 7.84–7.88 (m, 1H), 8.111 (d, J=4.6 Hz, 1H), 8.51–8.52 (m, 2H). K$_r$=0.4 nM.

EXAMPLE 6

This example describes the synthesis of [2S,3R,4S,5S]-2-[((N-[N-2-pyridinylmethyloxy)carbonyl ]anthranyl) amino]-5-[N-[3-hydroxyphenyl)carbonyl]amino]-3,4-dihydroxy-1,6-diphenylhexane (ND-4).

ND-4 was synthesized according to reaction Scheme VI of Example 1.

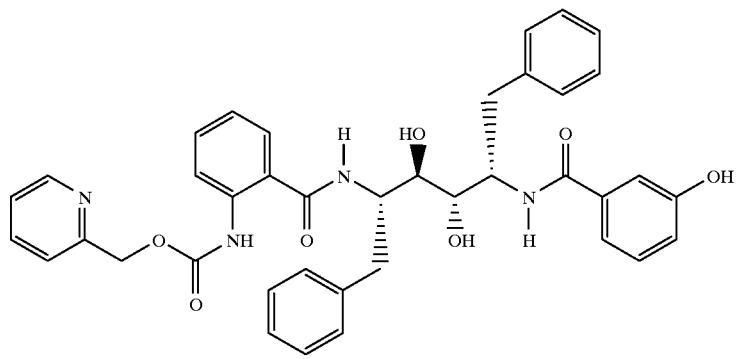

A solution of (2S,3R,4S,5S)-2-(N-tert-butyloxycarbonyl-amino)-5-amino-3,4-dihydroxy-1,6-diphenylhexane (Boc-DAD) (40 mg, 0.1 mmol), 3-hydroxybenzoic acid (15 mg, 1.15 mmol), HOBT (16 mg, 0.1 mmol), TBTU (32 mg, 0.1 mmol), in DMF (20 ml) was treated with DIPEA (26 mg, 35 μl, 0.2 mmol) and then stirred at room temperature for 4 hr. The solvents were removed under vacuum, and the residue was diluted with ethyl acetate, washed sequentially with a 10% solution of $KHSO_4$, water, and aqueous $NaHCO_3$, and dried over $MgSO_4$. Yield: 42 mg (80%).

This compound (42 mg) was dissolved in TFA (3 ml) and stirred at room temperature for 15 min. The volatiles were removed by evaporation under reduced pressure to provide the 3-hydroxy-benzamide-substituted DAD isostere as a TFA salt. The resulting compound was used in the next step without further purification.

A solution of (N-2-pyridinylmethyloxy)carbonyl)-anthranilic acid (Py-Ant, 24 mg, 0.09 mmol), the above-prepared DAD isostere (0.08 mmol), HOBT (13 mg, 0.08 mmol), and TBTU (26 mg, 0.08 mmol), in DMF (20 ml) was treated with DIPEA (30 mg, 42 μl, 0.2 mmol) and then stirred at room temperature for 6 hr. The solvents were removed under vacuum, and the residue was diluted with ethyl acetate, washed sequentially with a 10% solution of $KHSO_4$, water, and aqueous $NaHCO_3$, and dried over $MgSO_4$. Yield: 48 mg (71%) of crude ND-4 purified by preparative TLC using the solvent system EtOAc-hexanes (1:1).

EXAMPLE 7

This example describes the antiretroviral activity of compounds prepared in accordance with the above examples.

The inhibition constants ($K_i$) for the compounds of the above examples were determined using purified HIV-1 protease (wild-type, WT) (Tables I, II, IV and V) and R8Q and V82I mutant HIV-1 proteases (Table III). $K_i$ is an inhibition constant of a given compound as derived by enzyme kinetics. A low $K_i$ represents a high affinity of the compound for the enzyme, i.e., tight binding or low dissociation. Inhibition of the cleavage was assayed using a fluorogenic substrate available from Molecular Probes, Inc., Eugene, OR, and described in Kageyama et al., *Antimicrob. Agents. Chemother.*, 37, 272 (1993), and a fluorogenic substrate available from Bachem California, Torrance, Calif., and described in Kageyama et al. (1993), supra. The inhibitory potencies of these compounds are set forth in Tables I–V. Percent inhibition is the percentage inhibition of an enzyme's activity by a given compound at a given concentration.

TABLE I

Influence of substituents linked to the central core on in vitro activity.

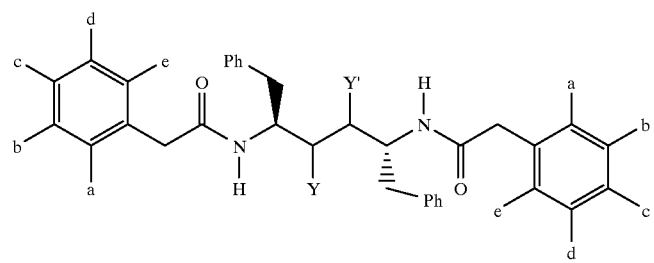

| No. | a | b | c | d | e | Y | Y' | % inhib* | $K_i$ |
|---|---|---|---|---|---|---|---|---|---|
| 5. | H | H | H | H | H | R—OH | S—OH | 38 | |
| 5a. | H | OH | H | H | H | R—OH | S—OH | | 3 μM |
| 5b. | OH | H | H | H | H | R—OH | S—OH | 66 | |

*% inhibition at 10 μM.
Ph = phenyl.

TABLE II

Influence of substituents linked to the central core on in vitro activity.

| No. | a | b | c | d | e | Y | Y' | % inhib* | $K_i$ |
|---|---|---|---|---|---|---|---|---|---|
| 6. | H | H | H | H | H | R—OH | R—OH | 55 | |
| 7. | H | OH | H | H | H | R—OH | S—OH | | 22 nM |
| 8. | H | OH | H | H | H | R—OH | R—OH | | 79 nM |
| 9. | H | OH | H | H | H | S—OH | S—OH | | 43 nM |
| 10. | H | H | OH | H | H | R—OH | R—OH | | 330 nM |
| 11. | OH | H | H | H | H | R—OH | R—OH | 66 | 10 μM |
| 12. | H | OH | OH | H | H | R—OH | S—OH | | 80 nM |
| 13. | H | OH | H | OH | H | R—OH | S—OH | | 0.7 μM |
| 14. | H | OH | H | $CH_3$ | H | R—OH | S—OH | | 1 μM |
| 15. | H | OH | H | H | $CH_3$ | R—OH | S—OH | | 75 nM |
| 16. | H | OH | $CH_3$ | H | H | R—OH | S—OH | | 132 nM |
| 17. | H | $NH_2$ | H | H | H | R—OH | S—OH | | 5 nM |
| 18. | H | OR* | H | H | H | R—OH | S—OH | 63 | |
| 19. | H | OR** | H | H | H | R—OH | S—OH | 9 | |
| 20. | N-2-(4-oxo-4H-1-benzopyran) | | | | | R—OH | S—OH | 67 | |
| 21. | N-2-(4-hydroxyquinoline) | | | | | R—OH | S—OH | 31 | |
| 22. | H | $NO_2$ | H | H | H | R—OH | S—OH | 40 | |
| 23. | -------------N-3-pyridinyl------------- | | | | | R—OH | R—OH | | 0.4 μM |
| 24. | H | OH | H | H | H | S—OH | H | | 25 nM |
| 25. | H | $NH_2$ | H | H | H | S—OH | H | | 6 nM |

R* = $CH_2CH_2OCH_2CH_2OCH_3$; R** = $CH_2CH_2OPh$.
*% inhibition at 10 μM.
Ph = phenyl.

TABLE III

Comparison of in vitro activity of selected compounds against R8Q and V82I mutants and wild-type HIV(w)

| No. | a | b | c | d | e | Y | Y' | Ki(nM) WT | R8Q | V82I |
|---|---|---|---|---|---|---|---|---|---|---|
| 7. | H | OH | H | H | H | R—OH | S—OH | 22 | 36 | 51 |
| 12. | H | OH | OH | H | H | R—OH | S—OH | 80 | 40 | 235 |
| 15. | H | OH | H | H | $CH_3$ | R—OH | S—OH | 75 | 89 | 54 |
| 17. | H | $NH_2$ | H | H | H | R—OH | S—OH | 5 | 20 | 109 |
| 24. | H | OH | H | H | H | S—OH | H | 25 | 34 | 96 |

Ph = phenyl.

TABLE IV
Anthranilamide-containing C2-Symmetric inhibitors of HIV protease.
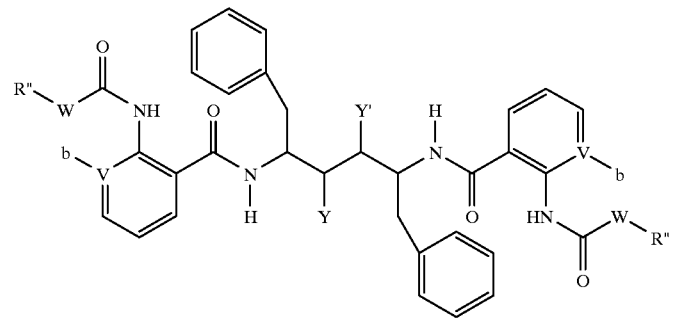
| No. | Y' | R" | W | b | V | $K_i$(nM) |
|---|---|---|---|---|---|---|
| 26. | OH | $CH_3$ | — | H | C | 41 |
| 27. | OH | $CH_2Ph$ | O | H | C | 2.4 |
| 28. | OH | $CH_2CH_3$ | O | H | C | 41% @ 10 μM |
| 29. | OH | OH | $CH_2$ | H | C | 41 |
| 30. | OH | $CH_2Ph$ | O | — | N | 3 |
| 31. | OH | $CH_2Ph$ | O | $CH_3$ | C | 12 |
| 32. | OH | $CH_2Ph$ | O | Cl | C | 91 |
| 33. | OH | $CH_2Ph$ | O | OH | C | 20 |
| 34. | OH | $CH_2$-2-Py | O | H | C | 0.06 |
| 35. | H | $CH_2Ph$ | O | H | C | 1.2 |
| 36. | H | $CH_2$-2-Py | O | H | C | 0.07 |
Ph = phenyl.
Py = pyridinyl.

TABLE V

| Name | Structure | Formula | M.W. | % Inhib. | Conc. | $K_i$ |
|---|---|---|---|---|---|---|
| DN-1 | 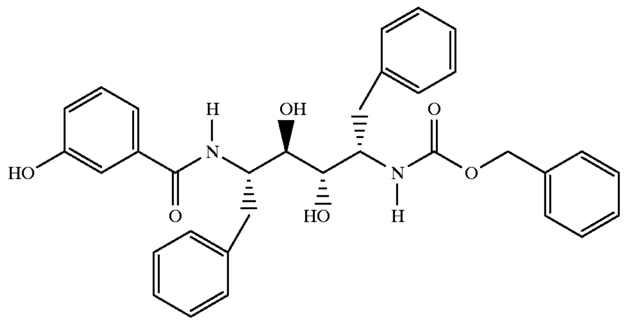 | $C_{33}H_{36}N_2O_6$ | 556 | | | $11.9 \pm 0.6$ nM |
| DN-4 | 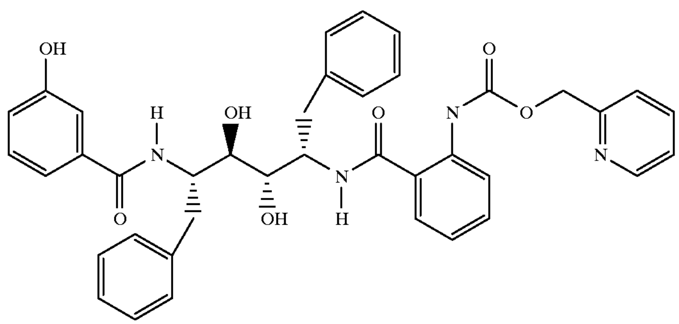 | $C_{39}H_{38}N_4O_7$ | 674 | | | $1.7 \pm 0.09$ nM |

TABLE V-continued

| Name | Structure | Formula | M.W. | % Inhib. | Conc. | $K_i$ |
|---|---|---|---|---|---|---|
| DN-5 | 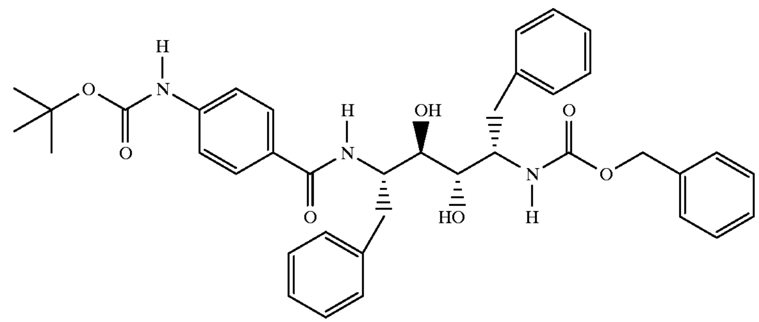 | $C_{39}H_{43}N_3O_7$ | 653 | | | 15.8 ± 1.3 nM |
| DN-6 | 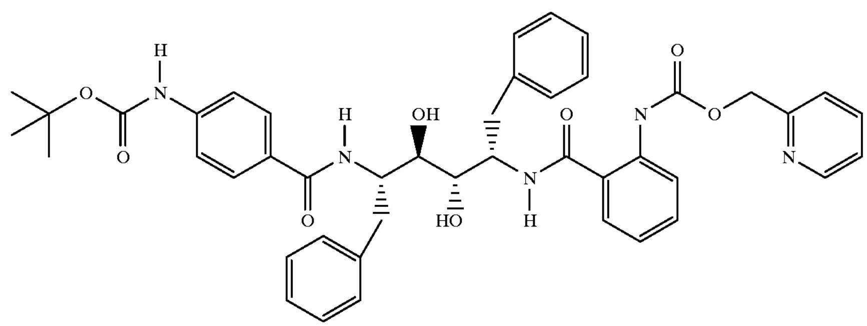 | $C_{44}H_{47}N_5O_8$ | 773 | 40%<br>15% | @ 10 nM<br>@ 1 μM | |

TABLE V-continued

| Name | Structure | Formula | M.W. | % Inhib. | Conc. | $K_i$ |
|---|---|---|---|---|---|---|
| DN-6B | 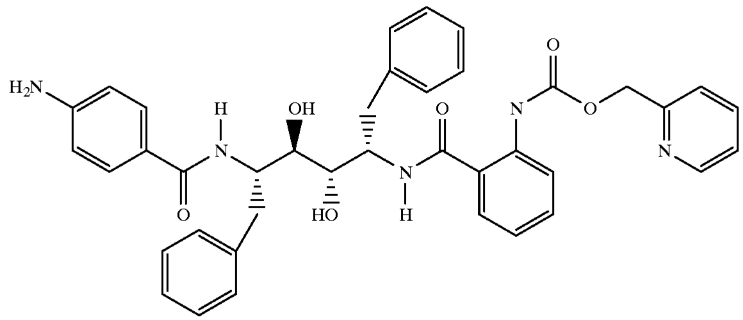 | $C_{39}H_{39}N_5O_6$ | 673 | | | 6.6 ± 0.3 nM |
| DN-10 | 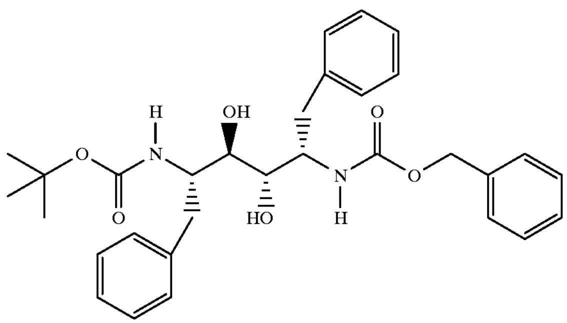 | $C_{31}H_{38}N_2O_6$ | 534 | | | 3.09 ± 0.007 nM |

TABLE V-continued

| Name | Structure | Formula | M.W. | % Inhib. | Conc. | $K_i$ |
|------|-----------|---------|------|----------|-------|-------|
| DN-11 | 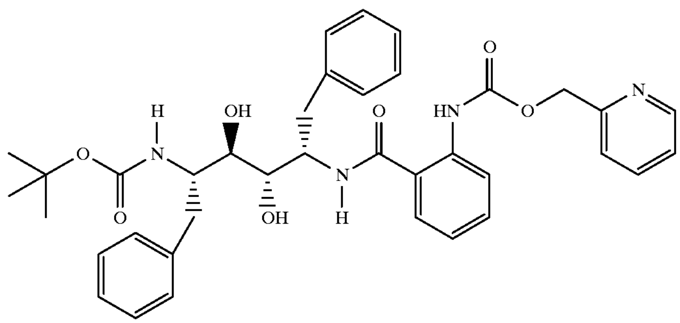 | $C_{37}H_{42}N_4O_7$ | 654 | | | 0.45 ± 0.1 nM |
| ND-4 | 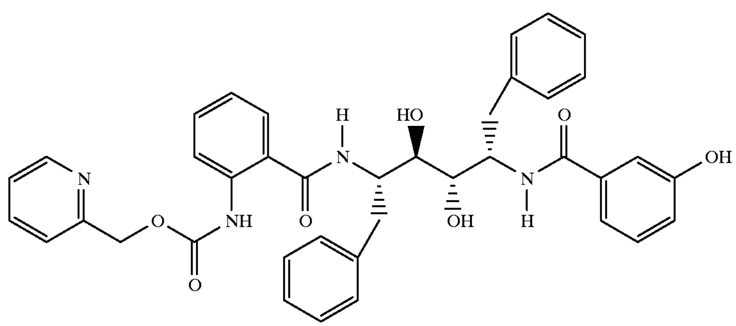 | $C_{39}H_{38}N_4O_7$ | 674 | | | 0.7 nM |

TABLE V-continued

| Name | Structure | Formula | M.W. | % Inhib. | Conc. | $K_i$ |
|---|---|---|---|---|---|---|

TABLE V-continued

| Name | Structure | Formula | M.W. | % Inhib. | Conc. | $K_i$ |
|------|-----------|---------|------|----------|-------|-------|

Compound 5 is a weak inhibitor of HIV PR. Compounds 5a and 5b, which possess 3-OH and 2-OH, respectively, show small improvements in inhibition of HIV PR. In contrast, incorporation of a hydrophilic group into the benzamide ring 6, in general, significantly improved inhibitory potency. As suggested by molecular modeling studies, the 3-hydroxy and 3-amino derivatives 7 and 17 ($K_i$ 22 nM and 5 nM, respectively) proved to be potent inhibitors of HIV PR. Consistent with the SAR studies of C2-symmetric diol-based inhibitors, the inhibitory potencies were dependent on the stereochemistry of the diol core (Kempf et al. (1990), supra). The 3,4 dihydroxy core possessing the R,S configuration was observed to be, in general, three times more potent than the core possessing the R,R configuration, as in compounds 7 and 8. The 2-methyl-5-hydroxy derivative 15, which by molecular modeling studies appears to possess a conformation in which the aromatic ring of the benzamide group is out of the amide plane, showed a $K_i$ of 75 nM. The 4-hydroxy derivative 10 showed a $K_i$ of 330 nM, whereas 2-hydroxy substitution 11 caused a dramatic loss in enzyme inhibitory potency (66% inhibition at 10 μM). The fusion of the second ring diminished binding of inhibitors (20 and 21) to the enzyme. The C2-symmetric compounds possessing a deshydroxy core have been shown to have improved binding affinities over the corresponding diols (Kempf et al. (1993), supra). Incorporation of the deshydroxy core, as in compounds 24 and 25, did not improve the inhibitory potencies (compare 7 vs. 24 and 17 vs. 25). Compound 26 was found to be an inhibitor of HIV PR with a $K_i$ of 41 nM. Compound 27, which possesses a benzyloxycarbonyl substituent, was 20 times more potent than compound 26, having a $K_i$ of 2.4 nM.

The inhibitory potencies of selected compounds against R8Q and V82I HIV PR mutants is shown in Table III. The R8Q mutation mostly affects the P3/P3' subsite on the enzyme, whereas the V82I mutation affects the S1/S1' subsite. Tested compounds were equipotent against both the wild-type (WT) and the R8Q mutant and 0.5–4-fold less effective against the V82I mutant. As predicted by molecular modeling studies, the 2-acylamino-benzamides, i.e., N-acyl anthranilamides, were very potent. Diol-48 (compound 34) had a $K_i$ of ~61 pM and DD-5 (compound 36) had a $K_i$ of ~74 pM.

EXAMPLE 8

This example demonstrates the anti-retroviral activity of the present inventive compounds in CEM cells.

Using the soluble formazan assay described by Weislow et al. (*J. Nat'l. Cancer Inst.*, 81, 577–586 (1989)), CEM cells chronically infected with HIV-1 were used to assay the anti-retroviral activity of Diol-48 (compound 34) and DD-5 (compound 36). The concentration of compound that inhibits 50% of viral activity ($EC_{50}$; determined as described in Weislow et al. (1989), supra) and the inhibition constant ($K_i$, as defined in Example 7) for the compound were determined. Diol-48 had a $K_i$ of 61 pM and an $EC_{50}$ of $3.2\times10^{-9}$M, whereas DD-5 had a $K_i$ of 74 pM and an $EC_{50}$ of $2.4\times10^{-9}$M. These results compared favorably with anti-retroviral compounds currently undergoing clinical trials. For example, KNI272, ABT538, Ro31-8959, and A77003 have $EC_{50}$ values of $4.2\times10^{-9}$M, $3.6\times10^{-8}$M (Flentge et al., *207th ACS Meeting*, San Diego, Calif. (1994)), $1\times10^{-8}$M (Ho et al., *J. Virol.*, 68, 2016 (1994), and $2\times10^{-7}$ (Ho et al., supra), respectively. In addition, compound DD-5 showed no toxicity even at doses as high as $10^{-4}$M and suppressed p24 synthesis at concentrations $\geq10^{-8}$M. These results show that the compounds of the present invention inhibit retroviral activity and have potential untility as retroviral inhibitors.

EXAMPLE 9

This example describes a novel method for selective protection of one of the $NH_2$ groups of DAD, which is the intermediate for synthesis for asymmetric compounds comprising anthranilamide and benzamide subunits.

To a stirred solution of DAD (1 g, 3.3 mmol) and triethylamine (0.5 ml, 3.6 mmol) in anhydrous $CH_2Cl_2$ (330 ml) under nitrogen was added benzyloxycarbonyl chloride (Z-Cl, 510 μl, 3.6 mmol in 25 ml $CH_2Cl_2$) by syringe pump at a rate of 2.5 ml/hr. After complete addition, the stirring was continued for an additional 4 hr. The organic layer was washed with 1% $KHSO_4$ (25 ml) and brine, dried over $MgSO_4$, and evaporated to provide 1.34 g (92%) of crude (2S,3R,4S,5S)-2-amino-5-(N-benzyloxycarbonylamino)-3,4-dihydroxy-1,6-diphenylhexane. The crude compound was dissolved in 25 ml ethyl acetate and treated with 25 ml of petroleum ether and stored at room temperature for 12 hr. The resulting precipitate was separated by filtration and the organic layer was concentrated under vacuum (1.27 g; 78%; HPLC (YMS-ODS-AQ, C-18 $CDCl_3$: δ 2.86 (dd, J=14,0.5 Hz, 1H), 2.92 (dd, J–14,7.5 Hz, 1H), 2.94 (dd, J=14,7.5 Hz, 1H), 3.17 (dd, J=14,7.5 Hz, 1H), 355 (dd, J=10,1.5 Hz, 1H), 3.70 (m, 1H), 3.82 (dd, J=10,3.5 Hz, 1H), 4.19 (ddd, J=9,7.5,1.5 Hz, 1H), 4.4–4.8 (bs, 2H), 4.98 (d, J=12.5 Hz, 1H), 5.06 (d, J=12.5 Hz, 1H), 6.43 (d, J=9 Hz, 1H), 7.18–7.33 (m, 15H), 7.99 (bs, 2H); MsFAB(M+H)$^+$435).

All publications cited herein are hereby incorporated by reference to the same extent as if each publication were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

What is claimed is:

1. A method of synthesizing 2S,3R,4S,5S-2-amino-5(N-benzyloxycarbonylamino)-3,4-dihydroxy-1,6-diphenylhexane, which method comprises the steps of:
   (a) reacting 2S,3R,4S,5S-2,5-diamino-3,4-dihydroxy-1,6-diphenylhexane and triethylamine with benzyloxycarbonyl chloride to form crude 2S,3R,4S,5S-2-amino-S-(N-benzyloxycarbonylamino)-3,4-dihydroxy-1,6-diphenylhexane; and
   (b) separating the reaction product.

* * * * *